United States Patent [19]

Klein et al.

[11] 4,142,053

[45] Feb. 27, 1979

[54] PROCESS FOR MANUFACTURING ALKYL-SUBSTITUTED β-RESORCYCLIC ACID ESTERS

[75] Inventors: Erich Klein; Frank Thömel; Hartmut Struwe, all of Holzminden, Fed. Rep. of Germany

[73] Assignee: Dragoco Geberding & Co. GmbH, Holzminden, Fed. Rep. of Germany

[21] Appl. No.: 827,427

[22] Filed: Aug. 24, 1977

[30] Foreign Application Priority Data

Nov. 23, 1976 [DE] Fed. Rep. of Germany ....... 2653177

[51] Int. Cl.[2] .............................................. C07C 69/88

[52] U.S. Cl. ...................................................... 560/67

[58] Field of Search .......................................... 560/67

[56] References Cited

FOREIGN PATENT DOCUMENTS 1416040 12/1975 United Kingdom ........................ 80/67

*Primary Examiner*—Paul J. Killos

*Attorney, Agent, or Firm*—Browdy and Neimark

[57] ABSTRACT

Synthetic oakmoss extracts of alkyl-substituted β-resorcylic acid esters useful as perfume ingredients, are prepared by refluxing alkyl-substituted dihydro-β-resorcylic acid esters with sulphuric acid and acetic anhydride, followed by saponifying the resultant diacetate.

11 Claims, No Drawings

PROCESS FOR MANUFACTURING ALKYL-SUBSTITUTED β-RESORCYCLIC ACID ESTERS

FIELD OF THE INVENTION

The present invention relates to the preparation of alkyl-substituted β-resorcylic acid esters.

BACKGROUND OF THE INVENTION

Natural oakmoss extracts are of fundamental importance to the perfume industry. They are used, for example, as important components of perfumes, "Chypre" and "Fougere" being noted.

Natural oakmoss is only available in limited quantities. Therefore, it is necessary to use synthetic substitutes with an oakmoss character. It is especially advantageous if the synthetic substances are naturally identical, i.e. components of natural oakmoss extract, and simultaneously exhibit the characteristic oakmoss aroma. For example, 3,6-dimethyl-β-resorcylic acid methyl ester is such an ingredient. It was first isolated from oakmoss oil by H. Waldbaum and A. Rosenthal/Ber. Duet. Chem Ges. 57B, 770 (1924)/.

A number of methods are known for preparing alkyl-substituted β-resorcylic acid esters from alkylated dihydro β-resorcylic acid esters. Dihydroresorcylic acid esters are readily obtained by condensation of α, β-unsaturated carboxylic acid esters with β-keto esters [cf. A. Sonn, Ber. Deut. Chem. Ges. 62B, 3012 (1929)] or by condensation of malonic acid esters with α, β-unsaturated ketones [cf. U. Steiner and B. Wilhelm, Helv. Chim. Acta 35, 1752 (1952)].

A. Sonn [Ber. Duet. Chem. Ges. 62B, 3012 (1929)] dehydrated dihydroresorcylates using expensive palladium catalyst. German Auslegeschrift No. 19 41041 and U.S. Pat. No. 3,634,491 of IFF Inc., New-York, describes oxidation with chlorine or chlorine-generating substances. Oxidation can also be performed with bromine in glacial acetic acid (U.S. Pat. No. 3,884,843, Fritzsche Dodge & Olcott Inc., N.Y.). The result is the dibromo-substituted aromate, which is dehalogenated with the aid of Raney nickel. However, the use of halogens or halogen-generating substances for oxidation requires special safety measures and special reactors, since these substances can have a toxic and poluting effect.

M. S. Kablaoui [J. Org. Chem. 39, 3696 (1974)] aromatized various substituted and unsubstituted cyclohexane-diones, heating them with a mixture of acetic anhydride and sulphuric acid. The reaction mechanism postulated by Kablaoui, however, would necessarily require a dione structure, so that transfer to structurally different classes of compounds does not appear possible.

SUMMARY OF THE INVENTION

However, in the course of an attempt to find a new route to the β-resorcylates, it was found that a conversion of the general Kablaoui type was possible with dihydro-β-resorcylates. There was no way that it could be predicted that the alkyl-substituted 2,4-diacetoxybenzoic acid ester (II) could be obtained in this manner with an approximately 50% yield. It was equally unexpected that saponification of these diacetates (II) produces the alkyl-substituted β-resorcylic acid ester (III) directly with a good yield. The carboalkoxy group proved to be surprisingly stable in the two partial processes.

Therefore, the process according to the invention for preparing the alkyl-substituted β-resorcylic acid ester which is used as oakmoss perfume consists of a simple two-stage process. In this process for the preparation of alkyl-substituted β-resorcylic acid esters (III), alkyl-substituted dihydro-β-resorcylic acid esters (I) are refluxed with a mixture of acetic anhydride and sulphuric acid after which the diacetate (II) produced by this process is saponified:

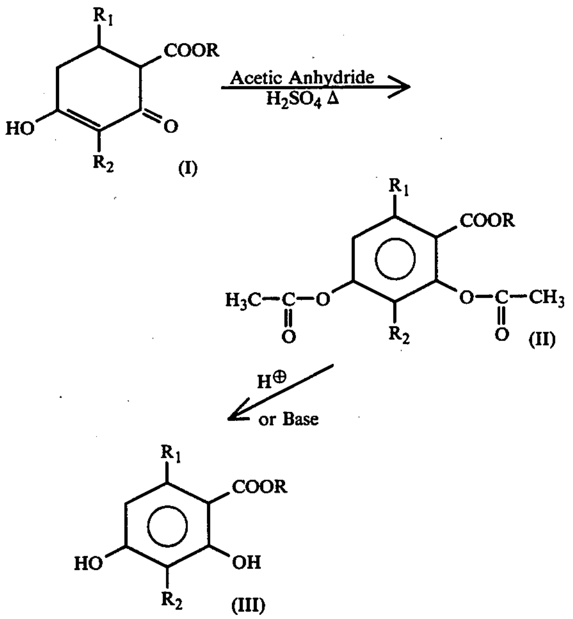

(I) (II) (III)

wherein R and $R_1$ are each alkyl with 1 to 3 carbon atoms, especially $CH_3$; and $R_2$ is alkyl with 1 to 3 carbon atoms, especially $CH_3$, or H.

It may be considered advantageous that only simple apparatus such as a stirrer and distillation are required. In addition, it is advantageous that no oxidizing agents are required which are expensive or which pollute the environment and endanger personnel responsible for carrying out the manufacturing process.

DETAILED DESCRIPTION OF EMBODIMENTS

It is useful to perform the reaction which produces diacetate (II) under a protective gas, e.g. an inert gas such as argon, or an inactive gas such as nitrogen. The dihydro-β-resorcylate (I) and an approximately equal amount of acetic anhydride are placed in a stirrer, and the molar equivalent of concentrated sulphuric acid which corresponds to the dihydro-β-resorcylate is added drop by drop for fifteen minutes. The acetic anhydride may serve as solvent in which case a five to tenfold molar excess of acetic anhydride may advantageously be used. The mixture is then refluxed and most of the unreacted acetic anhydride is distilled off under vacuum. The residue is poured carefully into hot water and extracted repeatedly with benzene. After neutralizing the benzene extract by washing with saturated sodium bicarbonate solution and water, the benzene is distilled off. The residue is distilled by fractional distillation.

The resultant diacetates (II) are dissolved in approximately ten times the amount of methanol, and saponified in the presence of p-toluene sulfonic acid by refluxing them for a number of days. The solvent is then distilled off, the residue dissolved in ether, agitated with sodium bicarbonate solution (in order to remove the resorcins), rinsed with water and then dried with anhydrous sodium sulphate. When the ether has been extracted under vacuum, the crude alkyl-substituted resorcylate is obtained, which can be re-crystallized from chloroform using activated charcoal.

Saponification can also be carried out as follows: The diacetate (II) is refluxed with twice the molar equivalent of sodium methanolate in a methanolate solution for three hours. The reaction mixture is then acidified with dilute sulphuric acid, extracted with ether, after which the ether phase is neutralized by rinsing with sodium bicarbonate solution and water, dried with anhydrous sodium sulphate, after which the solvent is distilled off under vacuum, producing resorcylate (III) as a crystalline residue.

The invention will be further described by the specific examples below:

Example 1

Preparation of 3,6-dimethyl-β-resorcylic acid methyl ester (β-orcinolcarboxylic acid methyl ester).

Using a stirrer with reflux condenser, dropping funnel, and internal thermometer, 164g (0.64 mol) of 3,6-dimethyl-β-dihydroresorcylic acid methyl ester and 1000 ml of acetic anhydride are mixed under argon. At 20° C., 64g (0.64 mol) of concentrated sulphuric acid are added drop by drop for fifteen minutes, whereupon the temperature of the reaction mixture rises to 40° C. The mixture is then agitated and refluxed for one hour, after which the excess acetic anhydride (650 ml) is distilled off at 5 torr until an internal temperature of 50° C. is reached. The residue is then carefully poured into 800 ml of hot water and extracted three times with 300 ml benzene each time. The combined benzene solutions are neutralized by washing twice with 200 ml each time of saturated sodium bicarbonate solution and with 200 ml of water each time.

After distilling off the solvent under vacuum, the residue is distilled by fractionation. At 184°–188° C. (5 torr) 83g (47% of the theoretical amount) of 2,4-diacetoxy-3,-6-dimethyl-benzoic acid methyl ester are distilled over, and it immediately crystallizes (melting point 87°–90° C.). The diacetate is dissolved in 960g of methanol, after which 5g of p-toluenesulfonic acid are added and then refluxed for 54 hours. After distilling off the solvent under vacuum, the residue is dissolved in 400 ml of ether, neutralized by washing twice with 100 ml each time of saturated sodium bicarbonate solution and once with 100 ml of water, then dried over anhydrous sodium sulfate, and the solvent is then distilled off. The result is 49.5g of crystalline, 3,6-dimethyl-β-resorcylic acid methyl ester. This crude product can be used directly as oakmoss perfume or can be re-crystallized from 250 ml of chloroform in the presence of 1.5g of activated charcoal. The result is 36.6g (63% of theoretical) pure product with a melting point of 142.5° to 144° C.

The structures of the end product and the diacetate were confirmed by infrared, NMR, and mass spectrometric analysis.

Example 2

Preparation of 6-methyl-β-resorcylic acid ethyl ester (orsellinic acid ethyl ester).

127g (0.64 mol) of 6-methyl-β-dihydroresorcylic acid ethyl ester, 1000 ml of acetic anhydride and 64g (0.64 mol) of concentrated sulphuric acid were prepared according to Example 1. The result was 128.3g (71.6% of theoretical) of 2,4-diacetoxy-6-methyl-benzoic acid ethyl ester (melting point 184°–186° C. at 2 torr). 120g (0.43 mol) of the diacetate were dissolved in 920g of ethanol and refluxed in the presence of 0.3g of p-toluenesulfonic acid for 24 hours. The solvent was then distilled off under vacuum. The crude product (103g) was re-crystallized from 200 ml of a mixture of benzene and petroleum ether (40° C.) mixed in the proportion of 9:1 using 5g of activated charcoal. The yield was 48g (55.8% of theoretical) of 6-methyl-β-resorcylic acid ethyl ester with a melting point of 127°–129° C.

It will be obvious to those skilled in the art that various changes may be made without departing from the scope of the invention and the invention is not to be considered limited to what is described in the specification.

What is claimed is:

1. A process for preparing a β-resorcylic acid ester of the formula:

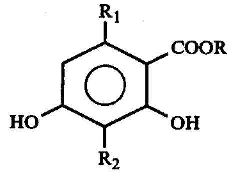

III wherein R and $R_1$ are each a $C_1$–$C_3$ alkyl and $R_2$ is a $C_1$–$C_3$ alkyl or hydrogen, comprising:

aromatizing the correspondingly substituted dihydro-β-resorcylic acid ester by heating approximately equal molar amounts of said dihydro-β-resorcyclic acid ester and sulfuric acid in the presence of at least an approximately equal molar amount of acetic anhydride to form the corresponding diacetate;

saponifying said diacetate according to alkaline or acid methods; and recovering said β-resorcylic acid ester.

2. A process according to claim 1 wherein the reaction which leads to said diacetate is carried out under a protective gas.

3. A process according to claim 1 wherein said sulphuric acid is added drop by drop in concentrated form to the above mixture of acetic anhydride and resorcylate at room temperature, and then the mixture is refluxed.

4. A process according to claim 3 wherein an excess of acetic anhydride is used and a majority of the unreacted acetic anhydride is then distilled off under vacuum.

5. A process according to claim 3 wherein the residue of said distillation is poured into hot water and the product extracted therefrom.

6. A process according to claim 1 wherein the saponification is performed with p-toluenesulfonic acid with reflux in a lower alkanol than the solvent.

7. A process according to claim 1 wherein the saponification is carried out with alkali alcoholate in an alcoholic solution with reflux.

8. A process according to claim 1 wherein said aromatization reaction is carried out in acetic anhydride as the solvent.

9. A process according to claim 8 wherein a five-to tenfold molar excess of acetic anhydride relative to resorcylate is used.

10. A process for preparing a β-resorcylic acid ester of the formula:

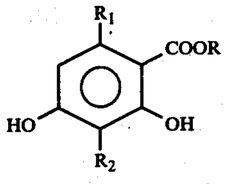

III wherein R and $R_1$ are each a $C_1$–$C_3$ alkyl and $R_2$ is a $C_1$–$C_3$ alkyl or hydrogen, comprising:

aromatizing the correspondingly substituted dihydro-β-resorcylic acid ester by heating approximately equal molar amounts of sulphuric acid and of said dihydro-β-resorcylic acid ester in the presence of an excess of acetic anhydride to form the corresponding diacetate;

distilling off under vacuum a majority of the unreacted acetic anhydride;

pouring the residue of this distillation into hot water and extracting the product therefrom;

saponifying said diacetates according to alkaline or acid methods; and recovering said β-resorcylic acid ester.

11. A process in accordance with claim 10 wherein said aromatizing is carried out at reflux temperature.

* * * * *